United States Patent [19]
Dyer et al.

[11] Patent Number: 6,087,400
[45] Date of Patent: *Jul. 11, 2000

[54] SURFACTANT-BASED ANTIMICROBIAL COMPOSITIONS AND METHODS FOR USING SAME

[75] Inventors: David L. Dyer, Cypress; Kenneth B. Gerenraich, Seal Beach, both of Calif.

[73] Assignee: Woodward Laboratories, Inc., Los Alamitos, Calif.

[ * ] Notice: This patent is subject to a terminal disclaimer.

[21] Appl. No.: 09/330,872

[22] Filed: Jun. 11, 1999

Related U.S. Application Data

[63] Continuation of application No. 08/972,613, Nov. 18, 1997, Pat. No. 5,994,383.

[51] Int. Cl.$^7$ ................................................. A01N 33/12
[52] U.S. Cl. ........................................ 514/643; 514/975
[58] Field of Search ................................ 514/643, 975

[56] References Cited

U.S. PATENT DOCUMENTS

| | | | |
|---|---|---|---|
| 2,577,773 | 12/1951 | Lambert | 252/152 |
| 3,419,006 | 12/1968 | King | 128/268 |
| 3,968,246 | 7/1976 | Merianos et al. | 424/330 |
| 4,203,872 | 5/1980 | Flanagan | 252/542 |
| 4,278,664 | 7/1981 | van Cleave | 424/148 |
| 4,321,277 | 3/1982 | Saurino | 424/329 |
| 4,336,151 | 6/1982 | Like et al. | 252/106 |
| 4,657,758 | 4/1987 | Goldenberg et al. | 434/49 |
| 4,721,724 | 1/1988 | Stettendorf et al. | 514/396 |
| 4,797,420 | 1/1989 | Bryant | 514/643 |
| 5,181,914 | 1/1993 | Zook | 604/307 |
| 5,284,833 | 2/1994 | McAnalley et al. | 514/23 |
| 5,346,692 | 9/1994 | Wohlrabet et al. | 424/61 |
| 5,362,422 | 11/1994 | Masters | 252/544 |
| 5,439,682 | 8/1995 | Wivell et al. | 424/401 |
| 5,550,163 | 8/1996 | Ding et al. | 514/643 |
| 5,661,170 | 8/1997 | Chodosh | 514/390 |

FOREIGN PATENT DOCUMENTS

| | | |
|---|---|---|
| 2108840 | 5/1983 | United Kingdom . |
| WO 87/03476 | 6/1987 | WIPO . |

OTHER PUBLICATIONS

Fisher, A.A., "Allantoin: A Non–Sensitizing Topical Medicament Therapeutic Effects of the Addition of 5 Percent Allantoin to Vaseline®", 1981, pp. 1–3.

Katz, N.D., "Tough as Nails . . . Fugoid® Tincture", *Cutis,* May 1992.

Sutton Laboratories, Inc., Fact Sheet on Allantoin, Jan. 1, 1992, pp. 1–6.

Allantoin Product Information, Published by Sutton Laboratories, Inc. (1992).

Germaben® II–E Product Information, Published by Sutton Laboratories, Inc. (1992).

Derwent Publications, Ltd., AN 84–154396, JP 59–059601 A, "Aqueous disinfectant composition—contg. N–alkyl dimethyl benzyl ammonium chloride and di:methyl ethyl benzyl ammonium chloride", Apr. 5, 1984, 1 page abstract.

Lubeck, D.P. et al, "Quality of life of persons with onychomycosis", *Quality of Life Res.,* 1993, 2, 341–348.

Petrocci, A.N. et al., *Proceedings of the 60th Mid–year Meeting of the Chemical Specialities Manufacturers Association,* 1974.

Drobeck, H.P., "Cationic surfactants: analytical and biological evaluation", Current topics on the toxicity of cationic surfactants, 1994, Chapter 3, Cross et al. Eds., Marcel–Dekker, Inc., New York.

*Primary Examiner*—Frederick Krass
*Attorney, Agent, or Firm*—Woodcock Washburn Kurtz Mackiewicz & Norris

[57] ABSTRACT

Antimicrobial compositions and methods for preparing and using same are provided. The antimicrobial compositions are surfactant-based and contain certain benzalkonium chloride homologs. The compositions are useful in treating infections in animals and humans, and can be applied to areas including the skin, nails, and mouth.

22 Claims, 5 Drawing Sheets

SURFACTANT-BASED ANTIMICROBIAL COMPOSITIONS AND METHODS FOR USING SAME

This application is a continuation of U.S. application Ser. No. 08/972,613, filed Nov. 18, 1997 and now U.S. Pat. No. 5,994,383.

FIELD OF THE INVENTION

This invention relates to surfactant-based antimicrobial compositions that deliver the active ingredients to target tissue (e.g., the mouth, mucous membranes, skin, and nails and adjacent tissue). The present invention also relates to methods of formulating these compositions and using the compositions.

BACKGROUND OF THE INVENTION

Recently, public attention to the area of personal hygiene has increased for a variety of reasons. One reason is the growing awareness that a majority of microbial pathogens (bacteria, fungi, yeast, molds and viruses) that cause disease in the human body gain access through various portals of entry (e.g., eyes, ears, nose, mouth), and that these microorganisms are generally introduced into these portals by the hands. In addition to this, various types of microorganisms that cause infections of the nail and skin are also acquired by direct contact with contaminated surfaces, both organic and inorganic, in the environment. It is therefore logical to conclude that a large number of illnesses may be prevented by the decontamination of the skin and hands, and of the major portal of entry into the body—the mouth.

It has been shown that at least 18% of the world population is afflicted with a microbial infection of the nail plate. Although such infections are more prevalent in third-world countries, there is also a substantial incidence of the infections in developed countries where personal hygiene standards are already high. Research has determined that the factors that constitute a predisposition to contracting such infections include a longer lifespan, increased therapies with antineoplastic agents, and a continually growing population of immunocompromised individuals. Historic treatment of these infections has had limited success; furthermore, physicians are reluctant to treat what has been generally perceived as merely a cosmetic disfiguration with a systemic medication.

Several studies have shown that infections of the nail cause a serious emotional and psychological impact on the affected individual. Patients with onychomycosis have lower ratings for mental and physical health, self esteem, social functioning, and for work-related activities than do their healthy, unafflicted counterparts. The economic impact of nail infections is great: in the 1989 fiscal year, Medicare claims alone totaled greater than 43 million dollars. Lubeck, D. P. Patrick, D. L. McNulty, P, Fifer, S. K., and Birnbaum, J. 1993. "Quality of life of persons with onychomycosis", Quality of Life Research. 2: 341–348.

Microbial infections of the nail are caused by many types of microorganisms. Importantly, nail infections often are the result of a microbial infection of the skin of the hand or foot. Dermal infections, such as body tineas, can spread to cause the much more pernicious conditions of onychia, paronychia, and onychomycosis (nail fungus). Therefore, it has been noted that effective treatments of such infections should also include proper preventative measures, namely, thorough sanitization of the skin of the hands and feet.

Treatment of the nail plate has historically included mechanical avulsion or chemical destruction, followed by application of topical or systemic antifingal agents. Examples of these types of medicaments are listed in Table I.

TABLE I

Antimicrobial Agents for skin and/or nail infections

| Application | Generic | Product | Manufacturer |
|---|---|---|---|
| A. Dermatophyte infections | | | |
| Topical: | Amorolfine | Loceryl | Roche |
| | Econazole-nitrate | Spectazole | Ortho-McNeill |
| | Naftifine | Naftin | Herbert Labs |
| | Oxiconazole | Oxistat | Glaxo-Wellcome |
| | Sulconazole | Exelderm | Westwood-Squibb |
| | Terbinafine | Lamisil | Novartis |
| | Tolnaftate | Tinactin | Schering-Plough |
| | Undecylinic acid | Desinex | Pharmacraft |
| | | Gordochrom | Gordon Labs |
| Oral: | Griseofulvin | Fulvicin | Schering-Plough |
| | Terbinafine | Lamisil | Novartis |
| B. Yeast infections | | | |
| Topical: | Nystatin | Mycostatin | Westwood-Squibb |
| C. Dermatophyte, yeast and bacterial infections | | | |
| Topical: | Ciclopirox olamine | Loprox | Hoechst-Roussel |
| | Clotrimazole | Lotrimin | Schering-Plough |
| | Econazole-nitrate | Spectazole | Ortho-McNeill |
| | Haloprogin | Halotex | Westwood-Squibb |
| | Miconazole | Micatin/ Monistat Derm | Ortho-McNeill |
| | | Fungoid Tincture | Pedinol |
| | Benzalkonium cholride | Mycocide NS Mone | Woodward Labs Kenlor Industries |
| D. (Saprophytes) Nondermatophytic filamentous opportunistic infections: cutaneous | | | |
| Topical: | Amphotericin B | Fungizone | Bristol-Myers Squibb |
| | Ketoconazole | Nizoral | Janssen |
| | Benzalkonium chloride | Mycocide NS Mone | Woodward Labs Kenlor Industries |
| Oral: | Fluconazole | Diflucan | Roerig-Pfizer |
| | Itraconazole | Sporanox | Janssen |
| E. Deep Mycotic infections: systemic | | | |
| Topical: | Amphotericin B | Fungizone | Bristol-Myers Squibb |
| | Ketoconazole | Nizoral | Janssen |
| Oral/IV: | Fluconazole | Diflucan | Roerig-Pfizer |
| | Itraconazole | Sporanox | Janssen |
| | Amphotericin B | Fungizone | Bristol-Myers Squibb |
| | Ketoconazole | Nizoral | Janssen |
| | Flucytosine | Ancobon | Roche |
| F. Actinomycetales Infections | | | |
| Antibacterial: | Amikacin | Amikin | Apothecon |
| | Ampicillin | Omnipen | Wyeth-Ayerst |
| | | Polycillin | Apothecon |
| | | Principen | Apothecon |
| | Penicillin-G | Bicillin | Wyeth-Ayerst |
| | | Wycillin | Wyeth-Ayerst |
| | Tetracycline | Doxycycline | Leaderle |
| | Trimethoprim | Bactrim | Roche |
| | Sulfamethoxazole | Septra | Glaxo-Wellcome |

Negative aspects associated with oral antifungal therapy for onychomycosis include their limited success rate, contraindications and drug interactions, toxicity, and the high cost of the medication. Furthermore, a general movement has begun in the scientific and medical communities away from the use of systemic antimicrobial therapy because the past indiscriminate and widespread use of broad-spectrum antibiotics has lead to an increase in the number of resistant strains of pathogenic microorganisms.

A variety of microorganisms are also present in the oral cavity. These range from the natural flora of the host to pathogenic species. Among these microorganisms are the gram-positive rods associated with the formation of plaque (a dense, enamel-adherant, microorganism-containing polysaccharide matrix). Even with good oral hygiene, it has been shown that microorganisms (including those responsible for plaque formation) rapidly build up in the oral cavity. Specific areas, including peridontal and subgingival spaces, and interpapillary spaces of the tongue present environments that that harbor bacteria. These species are difficult to reach by toothbrushing, and are only moderately affected by standard mouthwashes. The persistence of these microorganisms in such environments greatly increases the risk of calculus and plaque build up and carie formation, which in turn presents the danger of gingival inflammation and peridontal disease.

Although mouthwashes are standard in oral hygeine, they have generally been used to mask halitosis. Several mouthwashes that have been marketed for the reduction of bacteria and the prevention of plaque build up generally rely on a combination of alcohols (e.g. thymol, eucalyptol, ethanol; such as Listerine), or a combination of alcohols and a quaternary amine (e.g. ethanol, cetylpyridiniun chloride; such as Scope) or other oral surfactants (see U.S. Pat. No. 4,657,758), or of alcohol and chlorhexidine digluconate (Peridex from Proctor and Gamble). However, the use of alcohol containing formulations tends to produce unpleasant side effects including pain and stinging of the oral mucosa, foul aftertaste and discoloration of teeth. Prior art attempts to address this issue have included the development of alcohol-free formulations, the active ingredients of which vary. Compositions have included the use of a cetylpyridinium chloride in the presence of an oral surfactant (Lander Alcohol Free Mouthwash from The Lander Company, Inc.) and the use of stabilized chlorine (RetarDent from Rowpar). Because stabilized chlorine molecules are inactivated by interaction with proteins found in the mouth, they are unable to penetrate the occult, non-surface environments inhabited by microorganisms (see above) making these types of alcohol-free formulations of limited efficacy. In addition to this, these formulations sting open sores or cuts in the mouth.

Microbicidal surfactants, such as quaternary ammonium compounds, have certain advantages over other types of microbicides, including a relatively low toxicity against mammalian cells, but high toxicity against a wide spectrum of microbial pathogens when used at relatively low concentrations via the topical route of administration. Quaternary ammonium compounds possess surface-active properties, detergency, and antimicrobial properties including antimicrobial activity against bacteria, fungi, and viruses. The quaternary ammonium compounds possess little, if any, odor and have little or no deleterious effects on synthetic materials, such as rubber, plastics, ceramics, and steel. Furthermore, these biocides are biodegradable, and are less tainting than phenols. They also do not present the tissue-staining problems associated with the use of iodine. These intrinsic properties of cationic surfactants (as represented by quaternary ammonium compounds) have resulted in their inclusion in a variety of applications, and in a high level of popularity among users. The largest areas of application of quaternary ammonium compounds are for sanitization, preservation and disinfection.

The antimicrobial properties and medical uses of formulations containing quaternary ammonium compounds (QACs) in general, and specifically the compounds benzalkonium chloride, benzethonium chloride, methylbenzetho-nium chloride, and cetylpyridinium chloride, have been the subject of lenghty study by several U.S. FDA Panels on Antimicrobials (43 FR 1210, 56 FR 33644). These studies evaluated both the safety and efficacy of the compounds. It has been theorized that the biocidal activity of QACs involves the cationic charge on the amine group. This charge is attracted to negatively-charged protein moieties on the cell membrane of the microorgansim, and facilitates the adhesion of the QACs to the surface of the microorganism. This adhesion to anionic moieties of surface proteins disrupts tertiary and quaternary protein structure, thereby inactivating the protein. Furthermore, the hydrophobic moiety or moities of the QACs are intercalated into the lipid bilayer of the cell membrane causing leakage of the intracellular fluids, eventually killing the microorganisms.

Cationic mineral and organic molecules present in hard water compete with these negatively-charged proteins and greatly limit the ability of QACs to adhere to the cell membrane. In addition to this, the chemical incompatibility of QACs with anionic soaps and anionic detergents has been noted as another limitation to the potential application of QACs. These chemical enviroments thereby reduce the overall antimicrobial efficacy of this class of compounds.

One of the most commonly used QACs is benzalkonium chloride (BAC). It exhibits in vitro and in vivo microbicidal activity across a wide range of concentrations in aqueous solution and in alcoholic solvents. Prior art formulations employ BAC (USP grade) at 0.13% concentration with water as a solvent as a disinfectant for hospital utensils, environmental surfaces, metal instrumentation, catheters, ampules and thermometers (ZEPHIRAN CHLORIDE, Winthrop-Breon Laboratories, New York, N.Y.), and in combination with anti-inflamatories and/or anesthetics, as a topical first aid antiseptic (Bactine, Johnson & Johnson), or at higher concentrations such as 1:250 (w/w; 0.4%) in applications such as disinfectant towelettes, and 1:25 (w/w; 4.0%) for certain surface cleaners.

It is known that the chemical entity known as BAC represents a mixture of N,N-dimethyl alkyl amines, which conform generally to the formula:

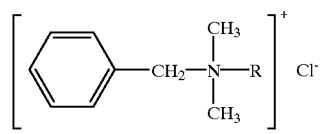

where R represents an alkyl side chain that can vary from 2 to 22 carbon atoms in length. In particular, the greatest microbicidal activity is believed to reside in the homologs with the n-alkyl side chain length in the range of 10–17 carbons. However, it is necessary to mix homologs together such that the sum of the carbon atoms in the alkyl side chains $(R_1+R_2+R_3+ \ldots R_n) \geq 21$–22 carbons in order to circumvent the activity-reducing effects of hard (cation containing) water. Accordingly, the United States Pharmacopaeia requires that the composition of commercially available BAC must be within the parameters of:

| | | |
|---|---|---|
| $N\text{-}C_{12}H_{25}$ | $\geq$ | 40.0% of total |
| $N\text{-}C_{14}H_{25}$ | $\geq$ | 20.0% of total |
| $N\text{-}C_{12}H_{25} + N\text{-}C_{14}H_{25}$ | $\geq$ | 70.0% of total |

This guideline has remained the industry standard since its inception in 1920–30, most likely due to the lack of development of an alternative system for the delivery of any single homolog as a discrete antimicrobial entity in antimicrobial applications. However, BAC mixtures of these species can contain an undefined set of BAC homologs, which may be present at concentrations as high as 30% of the total benzalkonium chloride species. Furthermore, the current methods of assay of N,N-dimethyl alkyl amines relies on the determination of the average alkyl side chain length of the mixture. Because of this, variation in lot-to-lot composition of BAC mixtures is possible, with the result that the antimicrobial effectiveness of the mixture and any reaction between the patient and the mixture may vary greatly, while the mixture still conforms to the USP specifications. From the above information it is apparent that an improvement over prior art uses of QACs, and BAC in particular, could be achieved if a delivery system could be developed that minimized the adverse effects to the activity of the QAC of hard water, anionic soaps, and anionic detergents, and dermal reactivity of susceptible patients. Likewise, all of the antimicrobial quaternary amine compositions, which, as does BAC, rely on the inclusion of inactive homologs for the preservation of activity in the presence of adverse environmental conditions, would benefit from such an invention.

SUMMARY OF THE INVENTION

Figure 1:
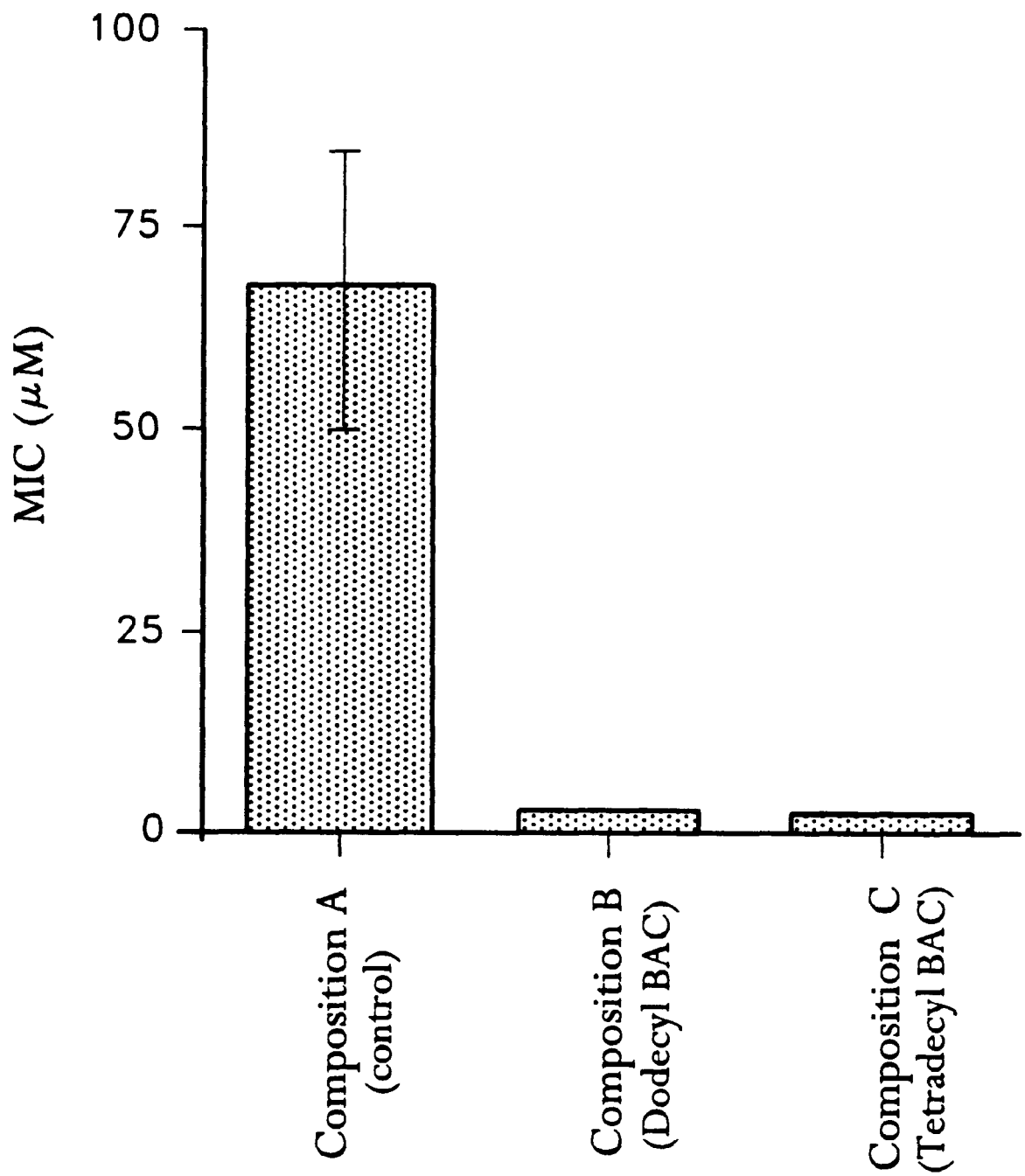
FIG. 1 shows the results of in vitro testing of antimicrobial activity of nail solutions containing benzalkonium chloride homologs as compared with the activity of solutions containing a USP benzalkonium chloride mixture.

In accordance with this need of the art, the present invention provides a surfactant-based, antimicrobial delivery system that minimizes the inactivation of quaternary ammonium compounds ("QACs"), in particular benzalkonium chloride ("BAC"), by hard water, anionic detergents, and anionic soaps, and that extends the microbicidal efficacy of the quaternary ammonium compound by minimizing interactions from other potentially competitive cations in the extracellular milieu. The present invention further provides methods for using the antimicrobial delivery system for treating infections and for preventing infections.

One aspect of the present invention is an improved antimicrobial, pharmaceutical composition for topical or oral administration, comprising:

(a) from about 0.05 to about 5 percent by weight benzalkonium chloride, wherein greater than about 90 percent by weight of the benzalkonium chloride is selected from the group of benzalkonium chloride homologs having the formula (I):

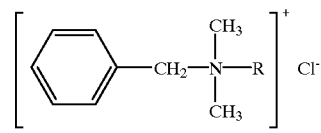

wherein R represents an alkyl side chain of from 12 to 14 carbon atoms;

(b) from about 0.05 to about 20 weight percent of a surfactant system comprising at least one nonionic, cationic or amphoteric surfactant; and (c) at least about 60 weight percent water.

Results of experiments show that the surfactant/emulsion system described in U.S. Pat. No. 5,661,170, assigned to Woodward Laboratories, Inc., has the unusual and unpredicted property of preserving the microbicidal efficacy of the BAC molecule, and of other quaternary amines, in part by masking and micellar entrapment of ionic species present in hard water. This property allows for the exclusion of any BAC homologs other than the most antimicrobially active ones, singly or in combination with others. The use of specific, most active BAC homologs in the context of this type of surfactant delivery system allows at least four improvements over prior art formulations.

First, the replacement of commercially available USP mixtures of BAC used in antimicrobial products with the same concentration of any one of the most antimicrobial BAC homologs, or combination of most active BAC homologs will significantly increase the in vitro and in vivo microbicidal activity of the products.

Second, the greater specific-antimicrobial-activity achieved for BAC in antimicrobial formulations wherein commercially-available USP mixtures of BAC is replaced with any single one of the most antimicrobial BAC homologs, or combination of most active BAC homologs, allows for the retention of the antimicrobial efficacy present in prior art formulations, but with the net reduction of the overall concentration of the benzalkonium chloride.

Third, cationic surfactants are generally recognized to be topical irritants. The primary dermal response in mammals to BAC is T-cell infiltration at the exposure site, indicating that an antigen-receptor mediated process is involved in the inflammation response. Drobeck, H. P. *Current topics on the toxicity of cationic surfactants*, Chapter 3 in "Cationic surfactants: analytical and biological evaluation." Cross, J. and Singer, E. J. Eds. Marcel-Dekker, Inc. New York. 1994. Therefore, a reduction in the total number of BAC molecules delivered in an antimicrobial solution will cause an overall decrease in the magnitude of the T-cell response at the site of exposure, and thereby lessen the irritative and inflammatory effects of BAC.

Fourth, in product applications where quaternary amines are introduced into the oral cavity, such as with a mouthwash, or swish-and-swallow preparation, the reduction of the overall BAC concentration also reduces the noxious side effects (i.e. bad and lingering taste, etc.) of this antimicrobial agent.

In preferred embodiments, the invention comprises an antimicrobial solution for nails, skin and surrounding tissue. This solution is comprised of nonionic, cationic, amphoteric and, to a very limited degree, anionic detergents alone or in combination with the active ingredient, which is a quaternary amine. The preferred quaternary amines include the most active antimicrobial homologs of benzalkonium chloride with respect to the compositional make-up of the antimicrobial composition of the present invention. Also present are excipients for the maintenance of a neutral pH, thickening agents, humectants, emulsification agent(s) and formulation stabilizers. Optional ingredients for this embodiment can include a cation chelator, supplemental amino acids, a keratolytic agent, a cell proliferant agent, and preservatives.

Another embodiment of the present invention includes a rinse-free handwash. This solution is comprised of nonionic, cationic, amphoteric and, to a very limited degree, anionic detergents alone or in combination with the active ingredient, which is a quaternary amine, most preferably the most active antimicrobial homologs of benzalkonium chloride. Also present are excipients for the maintenance of a neutral pH, thickening agents, humectants, emulsification agent(s) and stabilizers. Optional ingredients for this embodiment include a cation chelator, supplemental amino acids, a keratolytic agent, a cell proliferant agent, preservatives, humectants and fragrances.

Another embodiment of the present invention includes an antimicrobial mouthwash. This solution is comprised of nonionic, cationic, amphoteric and, to a very limited degree, anionic detergents alone or in combination with the active ingredient, which is a quaternary amine, most preferably the most antimicrobial homologs of benzalkonium chloride. Also present are excipients for the maintenance of a neutral pH, thickening agents, humectants, emulsification agent(s) and stabilizers. Optional ingredients for this embodiment include a cation chelator, supplemental amino acids, a keratolytic agent, a cell proliferant agent, preservatives, humectants, fragrances and flavoring agents.

The antimicrobial solutions of this invention may be applied to areas including, but not limited to, those indicated above, and, in the context of the surfactant delivery system, represent an improvement over prior art antimicrobial inventions. Further advantages and objectives of this invention will be apparent from the detailed description of the invention.

DETAILED DESCRIPTION OF THE INVENTION

The present invention provides an antimicrobial composition, a method of making the antimicrobial composition, and methods of using the antimicrobial composition. The antimicrobial compositions of the present invention are useful in effectively treating an existing microbial infection, such as an infection of the mouth, the skin, or the nails or adjacent tissue, and in preventing such infections. The antimicrobial compositions preferably contain as an active ingredient particularly antimicrobially active homologs of benzalkonium chloride (BAC). The antimicrobial compositions further contain a surfactant system that is believed to protect the antimicrobially active homologs of BAC from the deleterious effects of hard water, anionic detergents, surfactants, and soaps.

The antimicrobial compositions of the present invention are water-based systems that contain a biologically active antimicrobial agent or agents. The antimicrobial compositions also contain a surfactant system that contains at least one cationic, amphoteric, or nonionic surfactant. The antimicrobial compositions can also contain compounds that stabilize and solubilize the contents of the composition. The antimicrobial compositions can further contain various other compounds depending on the anticipated use for the composition.

The active agents that can be incorporated into the antimicrobial composition are the microbicidal quaternary amines in general, and preferably the most antimicrobially active BAC homologs, and other active antimicrobial agents that are compatible with the chemical formulation stated herein, and which are accepted for use as antimicrobial solutions at concentrations known to be effective and non-toxic for medical purposes.

In its preferred embodiment, the invention uses the BAC homologs that are defined by the formula (I):

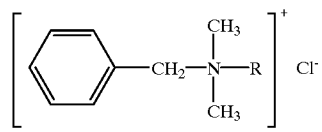

wherein R is an alkyl chain of from 10 to 17 carbon atoms, preferably from 10 to 15 carbon atoms, and more preferably from 12 to 14 carbon atoms. Specifically, these homologs include N,N-dimethyldecylammonium chloride, N,N-dimethylundecylammonium chloride, N,N-dimethyldodecylammonium chloride, N,N-dimethyltridecylammonium chloride, N,N-dimethyltetradecylammoniun chloride, N,N-dimethylpentadecylammonium chloride, N,N-dimethylhexadecylammonium chloride or N,N-dimethylheptadecylammonium chloride, alone or in conjunction with one or more of these most antimicrobially active homologs of BAC.

The antimicrobial compositions of the present invention that contain BAC will contain greater than about 85 weight percent, preferably greater than about 90 weight percent, more preferably at least about 95 weight percent, and even more preferably at least about 98 weight percent, of the BAC homologs defined by formula (1) where the total carbon atoms in the homologs are from 10 to 17, preferably from 10 to 15, and more preferably from 12 to 14. In certain preferred embodiments, the antimicrobial compositions will contain, in the stated concentrations, a BAC homolog defined by formula (I), having 12, 13 or 14 carbon atoms. The total content of BAC in the antimicrobial compositions of the present invention ranges from about 0.05 to about 5, preferably from about 0.01 to about 2.5, and more preferably from about 0.1 to about 2, weight percent, with the low and high values interchangeable between ranges. It is to be noted that all weight percents herein refer to the weight percent of that component with respect to the overall antimicrobial composition.

Other antimicrobial agents that are compatible with the antimicrobial composition include: monoalkyltrimethyl ammonium salts, dialkyldimethyl ammonium salts, heteroaromatic ammonium salts, polysubstituted quaternary ammonium salts, bis-quaternary ammonium salts, and polymeric quaternary ammonium salts. These compounds can be present in the antimicrobial composition in amounts ranging from about 0.05 to about 5.0 percent by weight, preferably from about 0.05 to about 2.5 percent, and more preferably from about 0.1 percent to about 2.0 percent by weight, based on the total weight of the composition.

The pH of the system is preferably maintained between about 3 and about 9, more preferably between about 5 and about 8. Quaternary ammonium compounds are in general chemically unstable below pH 3 or above pH 9, and are incompatible with anionic soaps and with moderate concentrations of anionic detergents. In particular, anionic soaps and surfactants have been found to neutralize quaternary ammonium compounds.

The antimicrobial compositions of the present invention preferably employ a particular surfactant system that is believed to protect the defined BAC homologs from the deletrious effects of hard water, anionic detergents, and soaps. The surfactant system contains cationic, nonionic and/or amphoteric surfactant agents that are chemically compatible with the active agents within the pH range stipulated above. Among others, examples of these surfactants include cocamidopropyldimethyl betaine (amphoteric), cocamidopropyl dimethyl betaine (non-ionic) and cetyltrimethyl ammonium chloride (cationic). There are many surfactants that may be grouped according to the three catgeories given above (see for example the text of McCutcheon's: Surfactants) that are chemically compatible and pharmaceutically acceptable that may be effectively used in this formulation. Exemplary cationic surfactants suitable for use according to the present invention are cetyl trimethyl ammonium chloride, trimethyl coco quaternary ammonium chloride, diquaternary polydimethylsiloxane, and trimethyl quaternary ammonium chloride. Exemplary suitable nonionic surfactants include alkanolamine, alkyldimethyl oxide, coconut monoethanolamine, cetyldimethylamine oxide, stearamine oxide, oleamine oxide, and cocamidopropylamine dimethyl oxide. Suitable amphoteric surfactants include cocamido betaine, oleyl betaine, cocamphdiacetate, cocamidopropylhydroxysultaine, and cocamidopropyldimethyl betaine.

In accordance with the present invention, the surfactant system is present in amounts from about 0.05 percent to about 20 percent, preferably from about 0.5 percent to about 15 percent, and more preferably from about 1 percent to about 10 percent by weight. The cationic surfactant, if used, is preferably present in an amount of from about 0.05 to about 5, preferably from about 0.5 to about 2.5, and more preferably from about 0.75 to about 1.5, weight percent. The nonionic surfactant, if used, is preferably present in an amount of from about 0.5 to about 8, preferably from about 1 to about 6, and more preferably from about 1.5 to about 3, weight percent. The amphoteric surfactant, if used, is preferably present in an amount of from about 0.5 to about 8, preferably from about 1 to about 6, and more preferably from about 3 to about 5, weight percent. In particular, a combination of surfactant types are used, such as a combination of cationic surfactant with anionic detergent, a combination of cationic surfactant with amphoteric surfactant, a combination of amphoteric surfactant with anionic detergent, or a combination of cationic surfactant, nonionic surfactant, and amphoteric surfactant, in the ranges specified. The use of more than one kind of surfactant within a type of surfactant is obviously contemplated, such as the use of two different kinds of cationic surfactants in a single formulation, which herein is encompassed by the reference to that type of surfactant in the singular form.

In addition to these surfactants, the inclusion of allantoin in quaternary ammonium compound formulations, such as Mycoside NS available from Woodward Laboratories, Inc., has been found to substantially improve the effectiveness of antimicrobial compositions. Allantoin can be used in the antimicrobial compositions in amounts ranging from about 0.01 percent by weight, based on the total weight of the composition, to about 10.0 percent, preferably from about 0.05 percent to about 5 percent, more preferably from about 0.25 percent to about 2.5 percent, and even more preferably from about 0.5 to about 1 percent.

It is also advantageous to incorporate a minor amount of amino acids in the formulation, particularly for use of the composition as a treatment for infections of the nail plate and surrounding tissue. In particular, those amino acids prevalent in keratin, including glutamine, glutamic acid, arginine, lysine and leucine can be used. Such amino acids can be used in amounts ranging from about 0.01 percent to about 1 percent by weight, based on the total weight of the composition, preferably from about 0.02 percent to about 0.5 percent.

An optional ingredient that can be added in the formulation is the class of anionic detergents that at low concentrations are chemically compatible with the antimicrobial composition in general. Although chemical inactivation of cationic quaternary amines occurs with moderate concentrations of anionic detergents, certain of the anionic detergents, such as polyethoxylated alkyl amines, are tolerated by cationic surfactants at low concentrations. These anionic detergents are useful as preservatives for the composition. Anionic detergents are preferably incorporated into the antimicrobial composition at ranges of from about 0.05 percent by weight to about 2.5 percent by weight, based on the total weight of the composition, more preferably from about 0.1 percent to about 2 percent by weight.

Another optional ingredient that can be added in the formulation is one or more compounds selected from the class of microbicidal ampholytes. These molecules are similar to cationic quaternary ammonium compounds with respect to microbicidal activity, and in their compatibility with nonionic and anionic detergents, but present the added benefit of being stable over a wider range of pH values. For example, microbicidal ampholytes can tolerate high levels of caustic soda. Examples of these molecules include ($C_{12}H_{25}NHCH_2COOH$), ($C_{12}H_{25}NH(CH_2)_2NHCH_2COOH$), and ($C_{12}H_{25}NH(CH_2)_2NH(CH_2)_2NHCH_2COOH$), where microbicidal activity generally increases as the number of nitrogen atoms increases. The inclusion of such antimicrobial agents is advantageous particularly in applications involving mouthwashes, where the pH of the solution should be greater than 7 to aid in plaque removal.

Other additives for the preservation of the antimicrobial active agent are common in pharmaceutical formulations and include preservatives. The most commonly used preservatives are the parabens (including, but not limited to methyl, ethyl, propyl, pentyl, hexyl and heptyl paraben), imidazolidinyl urea, diazolidinyl urea and the cis-isomer of 1-(3-chloroallyl)-3,5,7-triaza-1-azoniaadamantane (Quaternium 15). Such preservatives are preferably present in formulations according to the present application, either individually or as a sum total, in amounts of from about 0.01 weight percent to about 1 percent, based on the total weight of the composition, and more preferably from about 0.05 to about 0.75 weight percent.

Another optional ingredient which can be included in the antimicrobial composition is a compound selected from the various divalent and monovalent cation-chelating compounds. Cation chelators are widely used as preservative agents in many OTC pharmaceutical compounds. At the cellular level, the chelator sequesters divalent cations that are important for cell survival, such as calcium, from the lipid bilayer and from the cell interior. Lack of calcium alters the fluidity of the cell membrane, impairs calcium-dependent metabolic processes, and ultimately results in the death of the cell. Importantly, in the context of the other chemicals included in the invention, the cation chelator will also work to preserve the efficacy of ingredients such as, for example, cationic ingredients including surfactants, by protecting them from interference by cationic components of the non-formula, extracellular milieu. A substantial improvement of effectiveness of the preservative system will be obtained by the inclusion of EDTA, or other similar cation chelator compounds, such as ethylene glycol-bis(β-aminoethyl ether)-N,N,N',N'-tetraacetic acid (EGTA), 2,2'-(ethylenediimino)-dibutyric acid (EBDA) and nitrilo triacetic acid (NTA) in the antimicrobial compositions. The amount of cation chelator present, if used, is not critical but generally can be from about 0.01 weight percent to about 4.0 weight percent, based on the total weight of the composition, preferably from about 0.5 weight percent to about 1.5 weight percent.

Another optional ingredient that can be included in the antimicrobial compositions is a thickener. This is used for the stabilization of the final composition, and for the regulation of viscosity, which may vary widely according to the specific application (e.g., handwash, mouthwash, nail solution, etc.). Examples of chemically compatible thickeners or viscosity regulators include methylcellulose, hydroxypropylmethylcellulose, hydroxypropylcellulose, carboxymethylcellulose and methyl cellulose, among others, including lysophosphatidic acid. These compounds, if used, are present in minor amounts, generally from about 0.01 weight percent to about 4.0 weight percent, based on the total weight of the composition, preferably from about 0.5 to about 1.5 weight percent. Many forms of hydroxypropyl methyl cellulose (HPMC) are commercially available and may be used in preparing formulations according to the present invention. The various manufacturers provide instructions detailing the appropriate formulation procedures for specific types of HPMC.

Another optional ingredient that can be included in the compositions is a polyol co-solvent. This can be conveniently added for the dissolution or stabilization of certain ingredients. The polyol co-solvent is selected from the group of polyhydric alcohols such as propylene glycol or a polyethylene glycol. Such polyethylene glycols include the polyalkene glycol products with chemical structures having 2–3 carbons in the alkene moiety, and a mean molecular weight ranging from 200–4000. These compounds, if used, are present in amounts generally ranging from about 0.01 weight percent to about 15.0 weight percent, based on the total weight of the composition, preferably from about 0.5 weight percent to about 8.0 weight percent.

Other additives that can be incorporated into the compositions are those employed for the adjustment of pH, which are common throughout phramceutical formulations. These agents may be classified as organic and inorganic acids and bases alone or in combination with their respective salts. Commonly used acidifying agents are citric acid, sorbic acid, ascorbic acid, malic acid, succinic acid and so on. Commonly used alkalination agents include triethanolamine, ammonium hydroxide, potassium hydroxide, sodium hydroxide, etcetera. These pH adjustors are used in the amounts required to adjust the pH to the desired level, which amount is usually a relatively minor one.

The antimicrobial compositions of the present invention are water-based, and contain at least about 60 weight percent water, preferably from about 60 to about 95 weight percent, and more preferably from about 65 percent to about 95 percent water.

As noted above, the antimicrobial compositions of the present invention can be used for many purposes. One preferred use is to treat, and even prevent, microbial infections of the nail plate and surrounding tissue. Broad, preferred and optimal percentage ranges (on a weight percent basis, based on the total weight of the composition) for a typical antimicrobial composition for use in such treatment are given below, with water constituting the balance of the composition. Advantageously, the water content for such nail solutions is at least about 60 weight percent, preferably from about 65 percent to about 95 percent, and more preferably from about 85 to about 95 weight percent.

| Component | Broad | Preferred | Optimal |
|---|---|---|---|
| benzalkonium chloride homolog(s) | 0.05–5.0 | 0.10–2.5 | 0.1–2.0 |
| glyoxyldiureide | 0.05–5.0 | 0.25–2.5 | 0.5–1.0 |
| propylene glycol | 0.00–15.0 | 0.25–12.0 | 0.5–8.0 |
| hydroxypropyl methylcellulose | 0.00–4.0 | 0.25–2.0 | 0.5–1.5 |
| cocoamidopropyl dimethyl betaine | 0.5–8.0 | 1.0–6.0 | 3.0–5.0 |
| cocoamidopropyl dimethyl amine oxide | 0.5–8.0 | 1.0–6.0 | 1.5–3.0 |
| cetyl trimethyl ammonium chloride | 0.0–5.0 | 0.5–2.5 | 0.75–1.5 |
| cis isomer of 1-(3-chloroallyl)-3,5,7-triaza-1-azoniaadamantane chloride | 0.01–1.0 | 0.05–0.5 | 0.1–0.25 |
| diazolidinyl urea | 0.01–1.0 | 0.05–0.5 | 0.1–0.25 |
| triethanolamine | trace | trace | trace |
| citric acid | trace | trace | trace |

Other uses and applications for compositions prepared according to the methods of the present invention will be apparent to those skilled in the art. Exemplary uses include, but are not limited to, formulations for oral use such as a mouthwash or dentifrice; formulations for topical use such as a skin sanitizer, surgical scrub and preparation, and handwash; treatment of infections of the skin or mouth area in a human; veterinary medicament for animal skin, hooves, claws, fur, or teeth; nail paints and polishes; indwelling medical devices; venous access catheters; gastric and enteric long term feeding tubes; neurological shunting tubing; polytetrafluoroethane graft materials (both for tissue patch and vascular conduits); endotracheal and tracheostomy tubing; intravenous interarterial tubing; indwelling urinary catheters; joint implants; soft tissue implants, orthopaedic external fixation devices, (including hardware necessary to secure them to the bone); medication ampules; intravenous polyethylene fluid storage/delivery bag systems (including those for blood and blood products); mouth rinses (including swish and swallow preparations); skin preparations; bowel preparations; footwear inserts; and towelettes.

Compositions according to the present invention may also be used in formulations not intended for application or administration directly to a patient, such as, for example, a surface sanitizer, or environmental (e.g., air, water, surface) decontaminator.

In addition to the preferred homologs of BAC, other antimicrobial agents can be incorporated into the compositions of the present invention. These other compounds may be used in conjunction with the BAC homologs, and include the imidazole, triazole and other miscellaneous antimicrobial compounds. In addition to this, anesthetics may be used in conjunction with any of these formulations. Solubilization of these compounds in the context of the above antimicrobial compositions can be accomplished by using an appropriate mixture of water/polyol solvent. Broad, preferred, and optimal percentage ranges for these materials in weight percents are given below.

| Component | Broad | Preferred | Optimal |
|---|---|---|---|
| miconazole<br>1-[2-(2,4-dichlorophenyl)-2-[(2,4-dichlorophenyl)methoxyl)ethyl]-1H-imidazole | 0.5–5.0 | 1.0–3.0 | 1.5–2.5 |
| miconazole nitrate<br>1-[2,4-dichloro-b-{(2,4-dichloro-benzyl)oxy}pehnethyl]imidazole mononitrate | 0.5–5.0 | 1.0–3.0 | 1.5–2.5 |
| ketoconazole<br>cis-1-acetyl-4-[4-[[2-(2,4-dichloro-phenyl)-2-(1H-imidazol-1-ylmethyl)-1,3-dioxolan-4-yl]methoxy]-phenyl]piperazine | 0.5–5.0 | 1.0–3.0 | 1.5–2.5 |
| clotrimazole<br>1-o-chloro-a-a-diphenyl-benzyl)imidazole | 0.25–4.0 | 0.5–1.5 | 0.75–1.25 |
| econazole nitrate<br>1-[2-{(4-chlorophenyl)methoxy}-2-(2,4-dichlorophenyl)ethyl]-1H-imidazole mononitrate | 0.25–4.0 | 0.5–1.5 | 0.75–1.25 |
| oxiconazole nitrate<br>2',4'-dichloro-2-imidazol-1-ylacetophenone(Z)-[o-(2,4-dichloro-benzyl)oxime]mononitrate | 0.25–4.0 | 0.5–1.5 | 0.75–1.25 |
| isoconazole nitrate<br>1-[2,4-dichloro-b-(2,6-dichloro-benzyloxy)phenethyl]imidazole nitrate | 0.25–4.0 | 0.5–1.5 | 0.75–1.25 |
| itraconazole<br>4-[4-[4-[4-[[2-(2,4-Dichlorophenyl)-2-(1H1,2,4-triazol-1-ylmethyl)-1,3-dioxolan-4-yl]methocy]phenyl]-1-pipirazinyl]phenyl]-2,4-dihydro-2-(1-methyl-propyl)-3H-1,2,4-triazol-3-one | 0.25–4.0 | 0.5–1.5 | 0.75–1.25 |
| fluconazole<br>2,4-difluoro-a,a1-bis(1H-1,2,4-triazol-1-ylmethyl)benzyl alcohol | 0.25–4.0 | 0.5–1.5 | 0.75–1.25 |
| tolnaftate<br>O-2-naphthyl m,N-dimethylthio-carbanilate | 0.25–4.0 | 0.5–1.5 | 0.75–1.25 |
| naftifine hydrochloride<br>(E)-N-cinnamyl-N-methyl-1-naphthalenemethylamine hydrochloride | 0.25–4.0 | 0.5–1.5 | 0.75–1.25 |
| terbinafine hydrochloride<br>(E)-N-(6,6-dimethyl-2-hepten-4-ynyl)-N-methyl-1-naphthalene-methanamine hydrochloride | 0.25–4.0 | 0.5–1.5 | 0.75–1.25 |
| ciclopirox olamine<br>6-cyclohexyl-1-hydroxy-4-methyl-2(1H)-pyridone, 2-aminoethanol salt | 0.25–4.0 | 0.5–1.5 | 0.75–1.25 |
| haloprogin<br>3-iodoprop-2-ynyl 2,4,5-trichloro-phenyl ether | 0.25–4.0 | 0.5–1.5 | 0.75–1.25 |
| benzocaine<br>ethyl-p-amino-benzoate | 2.5–30.0 | 10.0–28.0 | 15.0–25.0 |
| lidocaine hydrochloride<br>acetamide 2-(diethylamino)-N-(2,6-dimethylphenyl)monohydrochloride | 0.5–10.0 | 1.0–7.5 | 0.5–10.0 |

Results presented below indicate that the microbicidal efficacy of an example antimicrobial nail solution formula containing a commercially available mixture of USP grade BAC is 50–100 fold less effective than a similar formula containing the same concentration of only the BAC homolog N,N-dimethyldodecylbenzyl ammonium chloride. A similar improvement was obtained when USP-grade BAC was substituted with only the N,N-dimethyltetradecylbenzyl ammonium chloride. As noted, the most preferred of the particular homologs include N,N-dimethyldodecylbenzylammonium-chloride, N,N-dimethyltridecylbenzylammonium-chloride, and N,N-dimethyltetradecylbenzylammonium-chloride.

An improved effectiveness in a mouthwash composition can be achieved if the quaternary amine, most preferably any one of the particular homologs N,N-dimethyldodecylbenzylammonium-chloride, N,N-dimethyltridecylbenzylammonium-chloride or N,N-dimethyltetradecylbenzylammonium-chloride, is administered in the context of a the antimicrobial composition of the present invention. For mouthwash compositions, the amount of quaternary amine can be from about 0.005 weight percent to about 2 percent, based on the total weight of the composition, preferably from about 0.09 to about 1 weight percent, and more preferably from about 0.1 to about 0.5 weight percent. In such formulations conventional additives may be used and the total amount of water present is from about 50 to about 97 weight percent, preferably from about 60 to about 96 percent, and more preferably from about 80 to about 95 percent.

Further, the use of the antimicrobial composition with the preferred homologs of BAC, particularly any one of the particular homologs N,N-dimethyldodecylbenzylammonium-chloride, N,N-dimethyltridecylbenzylammonium-chloride or N,N-dimethyltetradecylbenzylammonium-chloride, is highly effective as an antimicrobial handwash. For a handwash formulation, the amount of quaternary amine can be from about 0.005 to about 2.0 weight percent, preferably from about 0.05 to about 1.0 weight percent, and more preferably from about 0.06 to about 0.3 weight percent. The amount of water can be from about 50 to about 95 percent, preferably from about 60 to about 90 weight percent, and more preferably from about 70 to about 85 weight percent.

EXAMPLES

The following examples are merely illustrative of the present invention and should not be considered limiting of the scope of the invention in any way. These examples and equivalents thereof will become more apparent to those skilled in the art in light of the present disclosure and the accompanying claims.

Example 1

Formulation of Nail Solution

Solutions for treatment of nails were formulated using the following ingredients and quantities. Compositions A and B contain benzalkonium chloride homologs according to the invention. In Composition A, the BAC homolog is N,N-dimethyldodecylbenzyl ammonium chloride; in Composition B the BAC is N,N-dimethyltetradecylbenzyl ammonium chloride. Composition C is a control, containing a USP grade BAC mixture.

| FORMULATION:<br>Component | A<br>% (w/w) | B<br>% (w/w) | C<br>% (w/w) |
|---|---|---|---|
| H₂O (deionized distilled) | 92.94 | 92.94 | 92.94 |
| Quaternium 15 (100%) | 0.2 | 0.2 | 0.2 |
| Triethanolamine | qs | qs | qs |
| Hydroxypropylmethyl cellulose (100%) | 1 | 1 | 1 |
| Citric acid | qs | qs | qs |
| Cocamidopropyl dimethyl betaine (31%) | 1.16 | 1.16 | 1.16 |
| Cetyl trimethyl ammonium chloride (29%) | 0.29 | 0.29 | 0.29 |
| Cocamidopropylamine oxide (31%) | 0.7 | 0.7 | 0.7 |

-continued

| FORMULATION: Component | A % (w/w) | B % (w/w) | C % (w/w) |
|---|---|---|---|
| Quaternium 12 (50%) | 0.25 | 0.25 | 0.25 |
| Benzalkonium chloride component | 1.88 | 1.88 | 1.88 |
| Propylene glycol (56%) | 0.56 | 0.56 | 0.56 |
| Diazolidinyl Urea (40%) | 0.3 | 0.3 | 0.3 |
| Methyl Paraben (11%) | 0.11 | 0.11 | 0.11 |
| Propyl Paraben (3%) | 0.03 | 0.03 | 0.03 |
| Glyoxyldiureide (100%) | 0.5 | 0.5 | 0.5 |

The cis isomer of 1-(3-chloroallyl)-3,5,7-triaza-1-azoniaadamantane chloride (quaternium 15, available commercially as Dowicill 200) was dissolved into the water medium. Once it was dissolved, small amounts of hydroxypropyl methyl cellulose were then added and dispersed into the mixture. In a separate beaker the triethanolamine was dissolved in water to yield a dilute aqueous solution of the base. The aqueous triethanolamine solution was added dropwise to the stirred mixture to adjust the pH of the mixture within the range 8.0–10.0. Once the pH adjustment is achieved, the mixture was stirred until a transparent colorless solution is obtained. In a separate beaker the citric acid was dissolved in water to yield a dilute aqueous solution of the acid. The aqueous citric acid solution was added dropwise to the stirred mixture to adjust the pH of the mixture below 7. It is generally preferred to keep the pH within the range of 4.5 to 6.5.

Following this, the cocoamidopropyl dimethyl betaine, cocoamidopropyl dimethyl amine oxide and cetyl trimethyl ammonium chloride were added to the mixture while mixing at low to moderate speed. These compounds may be added in any order of sequence. The pH of the resulting mixture is adjusted to within the range pH 6.0–6.5; as necessary, by dropwise addition of aqueous solutions of citric acid and/or triethanolamine.

Propylene glycol was then added to the mixture while slowly stirring. The pH of the resulting mixture was adjusted to within the range pH 6.0–6.5, as necessary, by dropwise addition of aqueous solutions of citric acid and/or triethanolamine.

The desired benzalkonium chloride component for the composition (A, B, or C) was then slowly added to the mixture while slowly stirring. After the addition was complete, the pH of the resulting mixture was adjusted to within the range pH 6.0–6.5, as necessary, by dropwise addition of aqueous solutions of citric acid and/or triethanolamine.

Following this, the parabens and diazolinoyl urea, available together commercially as Germaben-IIE (a mixture of methyl paraben, propyl paraben and diazolinoyl urea in propylene glycol), were added slowly dropwise to the mixture with mixing at low speed. Upon addition to mixtures with low w/w propylene glycol/water ratios the parabens precipitated from the mixture forming a fine white powder like suspension. The mixture was stirred at slow to moderate speed until the parabens dissolved yielding a clear, colorless solution.

Small amounts of glyoxyldiureide were added and dispersed into the mixture while stirring at low to moderate speed. The mixture was stirred at slow to moderate speed until the glyoxyldiureide dissolved, yielding a clear colorless solution. The pH of the solution was adjusted to within the range pH 6.0–6.5, as necessary, by dropwise addition of aqueous solutions of citric acid and/or triethanolamine.

Surface treated HPMC (Dow Chemical Co., Midland, Mich.) was dispersed in aqueous medium and the pH of the mixture was then raised above pH 8.5 until a transparent colorless solution was obtained. (Non-surface treated HPMC may be used in place of surface treated HPMC, in which case the non-surface treated HPMC is first dispersed in aqueous medium, then the temperature of the mixture is adjusted upward (as per the manufacturer's instructions) and the mixture is stirred until a transparent colorless solution is obtained.) The resulting solution was then cooled to the appropriate temperature and the pH was adjusted, as necessary, by dropwise addition of aqueous solutions of citric acid and/or triethanolamine. Stable formulations were obtained following the preparation of these compositions.

Example 2

In Vitro Efficacy Testing of Compositions Prepared in Example 1

Minimum inhibitory concentration studies were performed using the gram-negative enterobacterium *Pseudomonas aerugenosa* (American Type Culture Collection #9027) in accordance with the protocol for testing the bactericidal activity of antimicrobial agents (Document M26-T of the National Center for Clinical and Laboratory Standards). *P. aerugenosa* were cultured overnight at 37° C. in trypsin soy broth to a final density of approximately $1 \times 10^8$ cfu/ml (0.5 McFarland standard) and then diluted 1:10 with cation-adjusted Mueller-Hinton medium. 10 microliters of this bacterial culture was then added to 200 microliters of an already-prepared dilution series of the test antimicrobial solution (Compositions A, B and C of Example 1). After a 5 minute incubation at room temperature, 10 microliters of wash test solution was plated onto a sector of a Letheen-agar plate and incubated at 37° C. overnight. MIC breakpoint was interpreted as the highest dilution for which no growth was evident.

The results (see FIG. 1) showed that Compositions A and B, containing either the $C_{12}$ or the $C_{14}$ BAC homolog (homolog of Formula I, wherein R has either 12 or 14 carbon atoms), were far more effective in vitro at inhibiting the growth of *P. aerugenosa* than was Composition C, which contained the USP benzalkonium chloride mixture.

Example 3

Preparation of Handwash

A handwash formulation was prepared according to the following formula:

| Component | % w/w |
|---|---|
| H₂O (deionized distilled) | 96.1 |
| Quaternium 15 (100%) | 0.2 |
| Triethanolamine | qs |
| Hydroxypropylmethyl cellulose (100%) | 0.25 |
| Citric acid | qs |
| Cocamidopropyl dimethyl betaine (31%) | 0.62 |
| Cetyl trimethyl ammonium chloride (29%) | 0.41 |
| Cocamidopropylamine oxide (31%) | 0.31 |
| Quaternium 12 (50%) | 0.4 |
| Benzalkonium chloride component (50%) | 0.13 |
| Propylene glycol (56%) | 0.56 |
| Diazolidinyl Urea (40%) | 0.3 |
| Methyl Paraben (11%) | 0.11 |
| Propyl Paraben (3%) | 0.03 |

-continued

| Component | % w/w |
|---|---|
| Glyoxyldiureide (100%) | 0.5 |
| Methyl salicylate (100%) | 0.025 |
| Cineole (100%) | 0.075 |

The BAC component was a homolog of Formula I wherein R has 14 carbon atoms. The procedure used was the same as in Example 2. A stable handwash composition was obtained.

Example 4

In Vitro Efficacy Testing of Handwash Prepared in Example 3

Minimum inhibitory concentration studies were performed using microorganisms that are involved in nosocomial infections: *Pseudomonas aerugenosa* (American Type Culture Collection #9027), *Staphylococcus aureus* (American Type Culture Collection #6538), *Enterococcus faecalis* (American Type Culture Collection #49452) and *Candida albicans* (American Type Culture Collection #10231) in accordance with the protocol for testing the bactericidal activity of antimicrobial agents (Document M26-T of the National Center for Clinical and Laboratory Standards).

Figure 2:
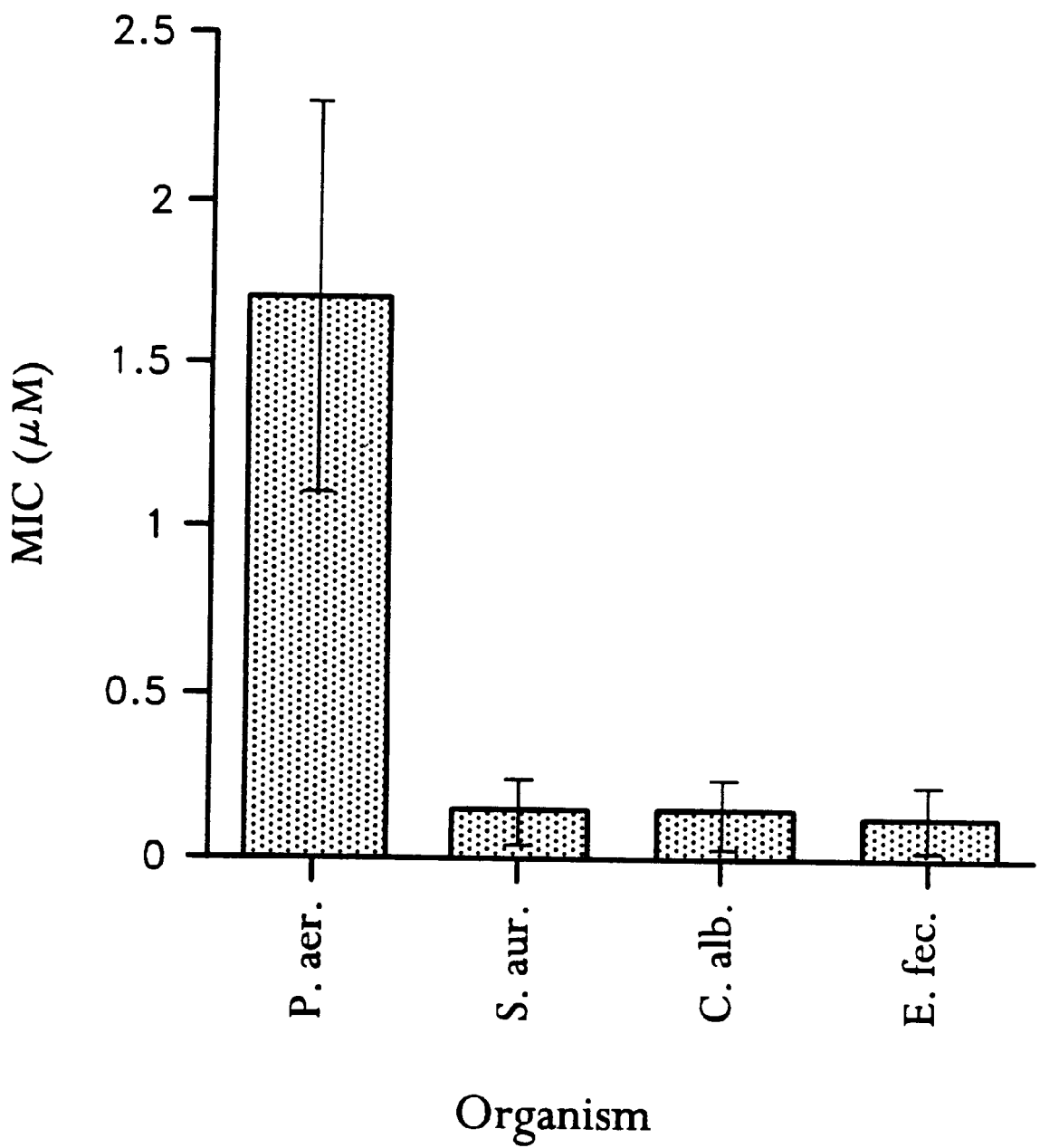
FIG. 2 shows the results of in vitro testing of antimicrobial activity of handwash solutions of the present invention, containing benzalkonium chloride homologs, against four microorganisms.

Microorganisms were cultured overnight at 37° C. in trypsin soy broth to a final density of approximately $1 \times 10^8$ cfu/ml (0.5 McFarland standard) and then diluted 1:10 with cation-adjusted Mueller-Hinton medium. Ten microliters of the culture was then added to 200 microliters of an already-prepared dilution series of handwash formulation prepared according to Example 3. After a 5 minute incubation at room temperature, 10 microliters of each test solution was plated onto a sector of a Letheen-agar plate and incubated at 37° C. overnight. The MIC breakpoint was interpreted as the highest dilution for which no growth was evident. The results (see FIG. 2) show that the handwash is effective at killing yeast and the Gram-negative and Gram-positive bacteria tested. Since the handwash formulation is intended for use without rinsing, we also tested its effectiveness in this context. Similar results were obtained with and without water-rinsing.

Example 5

Comparison of Efficacy of Handwash Prepared in Example 3 with Efficacy of Ethanol-Based Handwash Formulations Handwash prepared according to Example 3 was tested for efficacy in comparison to commercially-available ethanol-based handwash formulations. The following formulations were tested according to the protocol given in the *Federal Register*, Volume 59(116), Jun. 17th, 1994, 21CFR 333.470: "Effectiveness testing of an antiseptic handwash or healthcare antiseptic handwash"; CoolBlue, Creative Nail Design, Inc.® (62% ethanol); Derma Stat, Jones Medical Industries (65% ethanol); Swiss Guard®, OPI Products® (67% ethanol); TLC Alcohol Foam Scrub, Polychem Corporation (70% ethanol).

Volunteers for the study were consecutively contaminated ten times over the course of 2.5 hours with 5 ml of *Serratia marcescens* (ATCC 14756). After each contamination and subsequent drying period, volunteers were asked to wash their hands for 2 minutes with 5 ml of the test compound. Following washing, viable organisms remaining on the hands were collected by placing hands in rubber gloves each containing 25 ml of Butterfield's phosphate buffer, and washing this fluid over the hands for 2 minutes. Following this, a portion of the wash fluid containing organisms was plated onto trypsin soy agar plates. Growth was assessed after incubation overnight at room temperature.

The results show that the number of residual bacteria present after washing using a non-antimicrobial hand soap (baseline count) was far greater than the number of residual bacteria observed after the contamination/wash with either a commercially-available solution of 70% ethanol or with the handwash formulation cited in Example 3.

Figure 3:
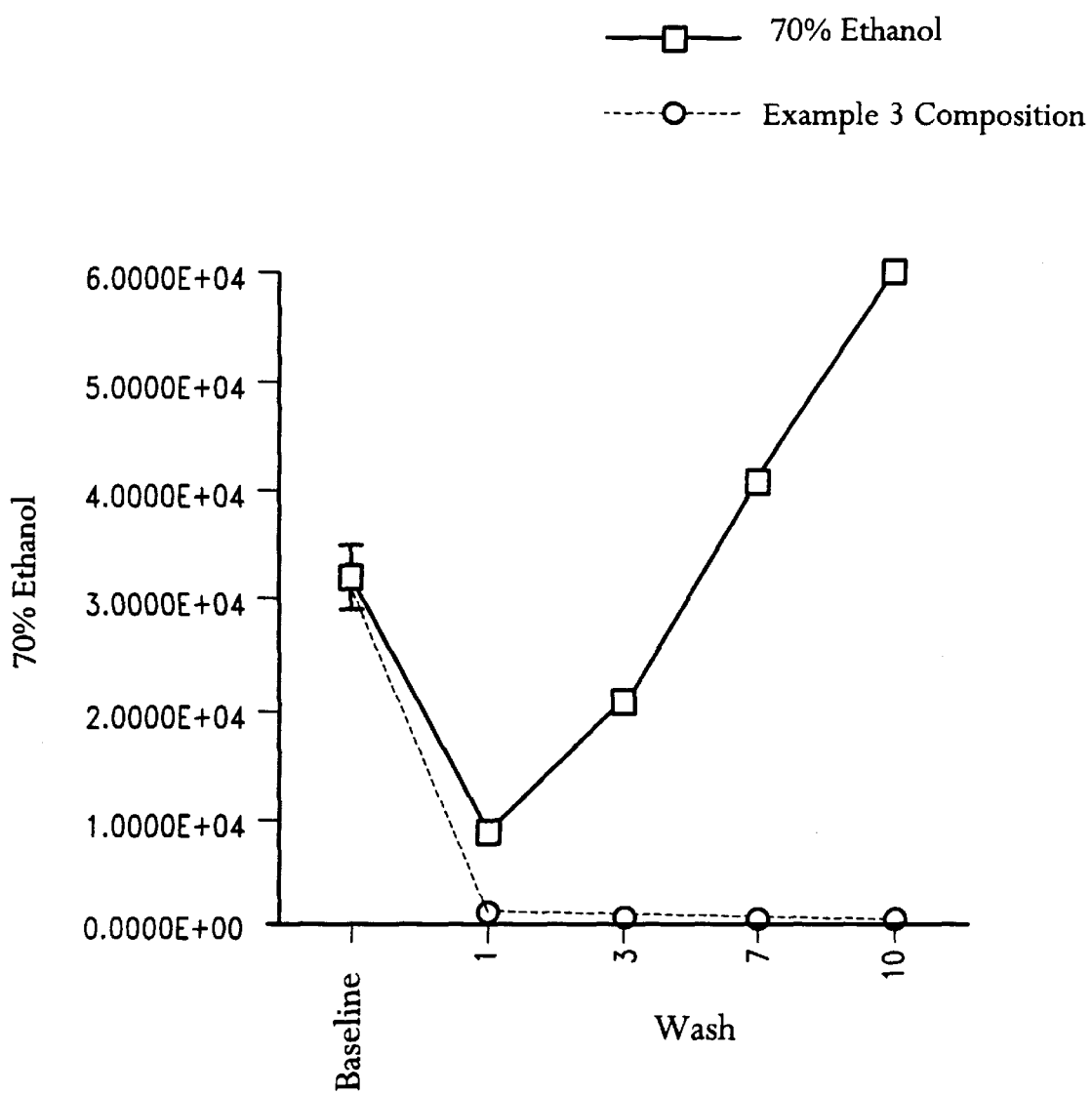
FIG. 3 shows the results of comparative testing of the efficacy of handwash solutions of the present invention and commercially available ethanol-based handwash formulations against *Serratia marcescens*.

Unexpectedly, the residual number of bacteria present after consecutive washes with the ethanol-containing product increased greatly (see FIG. 3). In contrast, the residual number of colonies present after washing with the example handwash cited in Example 3 decreased markedly, such that after the 10th wash, remaining bacteria were at 0–0.01% of the baseline count; in contrast, after the 10th wash with the ethanol containing product, remaining bacteria were at 130–200% of the baseline count. Overall, these unexpected findings indicate the superior efficacy of the handwash formulation prepared according to Example 3 over a commercially-available, federally-accepted antimicrobial formulation.

Example 6

Preparation of Mouthwash

A mouthwash was prepared according to the following formula:

| Component | % (w/w) |
|---|---|
| H₂O (dd) | 83.15 |
| Quaternium 15 (100%) | 0.01 |
| Triethanolamine | qs |
| Hydroxypropylmethyl cellulose (100%) | 0.125 |
| Citric acid | qs |
| Cocamidopropyl dimethyl betaine (31%) | 0.2 |
| Cetyl trimethyl ammonium chloride (29%) | 0.05 |
| Cocamidopropylamine oxide (31%) | 0.1 |
| Quaternium 12 (50%) | 0.025 |
| Benzalkonium chloride homolog (50%) | 0.094 |
| Propylene glycol (56%) | 0.028 |
| Diazolidinyl Urea (40%) | 0.02 |
| Methyl Paraben (11%) | 0.0055 |
| Propyl Paraben (3%) | 0.0015 |
| Glyoxyldiureide (100%) | 0.025 |
| Cetylpyridinium chloride | 0.67 |
| Sorbitol | 15 |
| Methyl salicylate | 0.3 |
| FD&C Green #3 (0.4% solution) | 0.15 |

The BAC homolog was a homolog of Formula I wherein R had 14 carbon atoms. The components were formulated as in Example 1. A stable mouthwash formulation was obtained.

Example 7

MIC Determination For Mouthwash Prepared in Example 6

Minimum inhibitory concentration studies were performed using microorganisms that are known to cause nosocomial infections: *Pseudomonas aerugenosa*

(American Type Culture Collection #9027), *Staphylococcus aureus* (American Type Culture Collection #6538), *Enterococcus faecalis* (American Type Culture Collection #49452) and *Candida albicans* (American Type Culture Collection #10231) in accordance with the protocol for testing the bactericidal activity of antimicrobial agents (Document M26-T of the National Center for Clinical and Laboratory Standards).

Microorganisms were cultured overnight at 37° C. in trypsin soy broth to a final density of approximately $1 \times 10^8$ cfu/ml (0.5 McFarland standard) and then diluted 1:10 with cation-adjusted Mueller-Hinton medium. 10 microliters of the culture was then added to 200 microliters of an already-prepared dilution series of the mouthwash formulation prepared according to Example 6. After a 5 minute incubation at room temperature, 10 microliters of each test solution was plated onto a sector of a Letheen-agar plate and incubated at 37° C. overnight. MIC breakpoint was interpreted as the highest dilution for which no growth was evident. The results show that the mouthwash is effective at killing yeast and the Gram-negative and Gram-positive bacteria tested.

Figure 4:
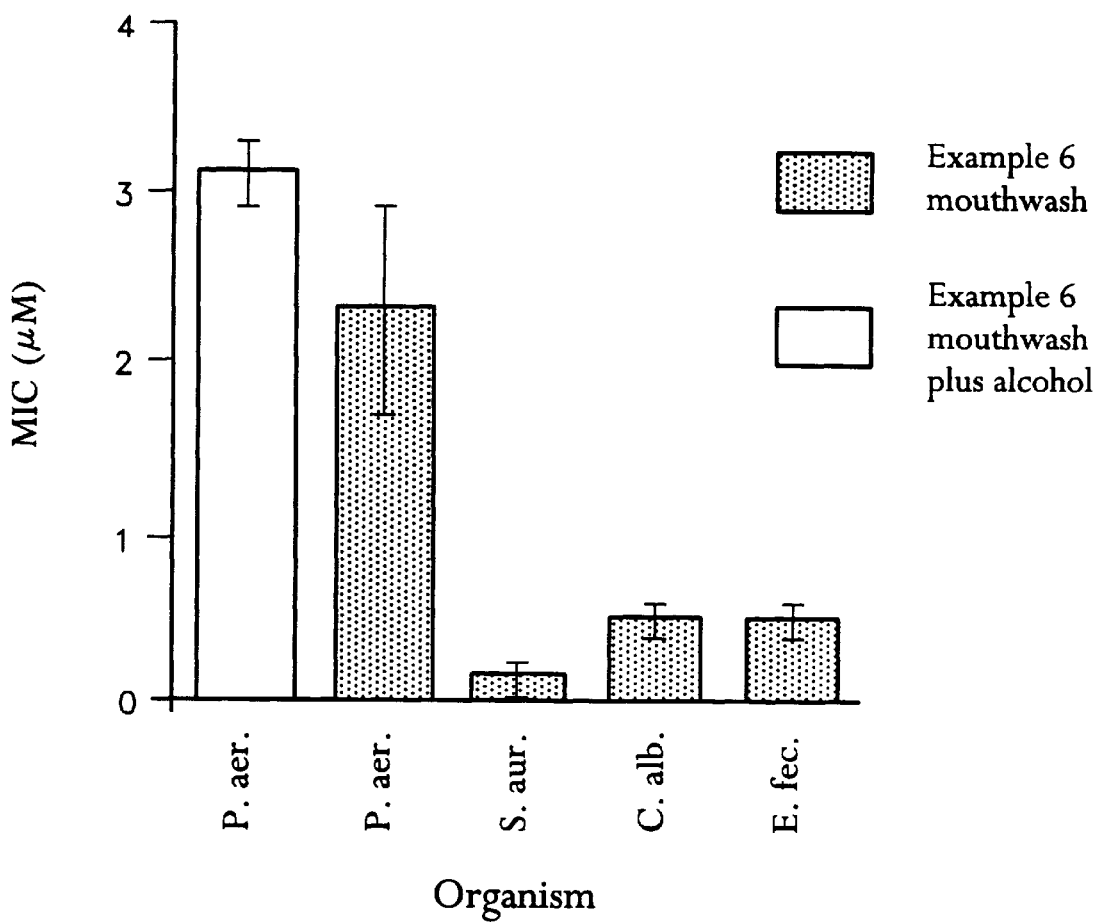
FIG. 4 shows the results of testing of the efficacy of mouthwash solutions of the present invention against four microorganisms. Efficacy is also shown for a mouthwash solution containing a benzalkonium homolog and added alcohol.

A subsequent experiment was conducted to determine the MIC breakpoint for *P. aerugenosa* for a mouthwash of the type indicated in Example 6, but with the addition of SD alcohol to the mixture of quaternary amines and surfactants. The results (see FIG. 4) show that this example solution is also effective against this Gram-negative organism, indicating that alcohol is compatible with the formulation stated herein.

Example 8

Test of Population Reduction of Oral Cavity Microorganisms Using Antimicrobial Mouthwash Prepared in Example 6.

To determine the efficacy of the mouthwash in vivo at reducing the number of bacteria in the oral cavity, test subjects were asked not to brush their teeth or use any other mouthwash for 2 hours prior to the testing. Tests were carried out by having each volunteer place 30 ml of the test solution under study (either a non-antimicrobial phosphate collection buffer, the mouthwash prepared according to Example 6, or the commercially-available stabilized chlorine dioxide RetarDent mouthrinse) in their mouth, and swish the material to thoroughly wet the teeth, gums and tongue, for 30 seconds. After this rinse period, the mouthwash was collected and a small portion was plated on a Trypsin Soy Agar plate. Bacterial growth was assessed after 24 hours of incubation at 37° C.

Figure 5:
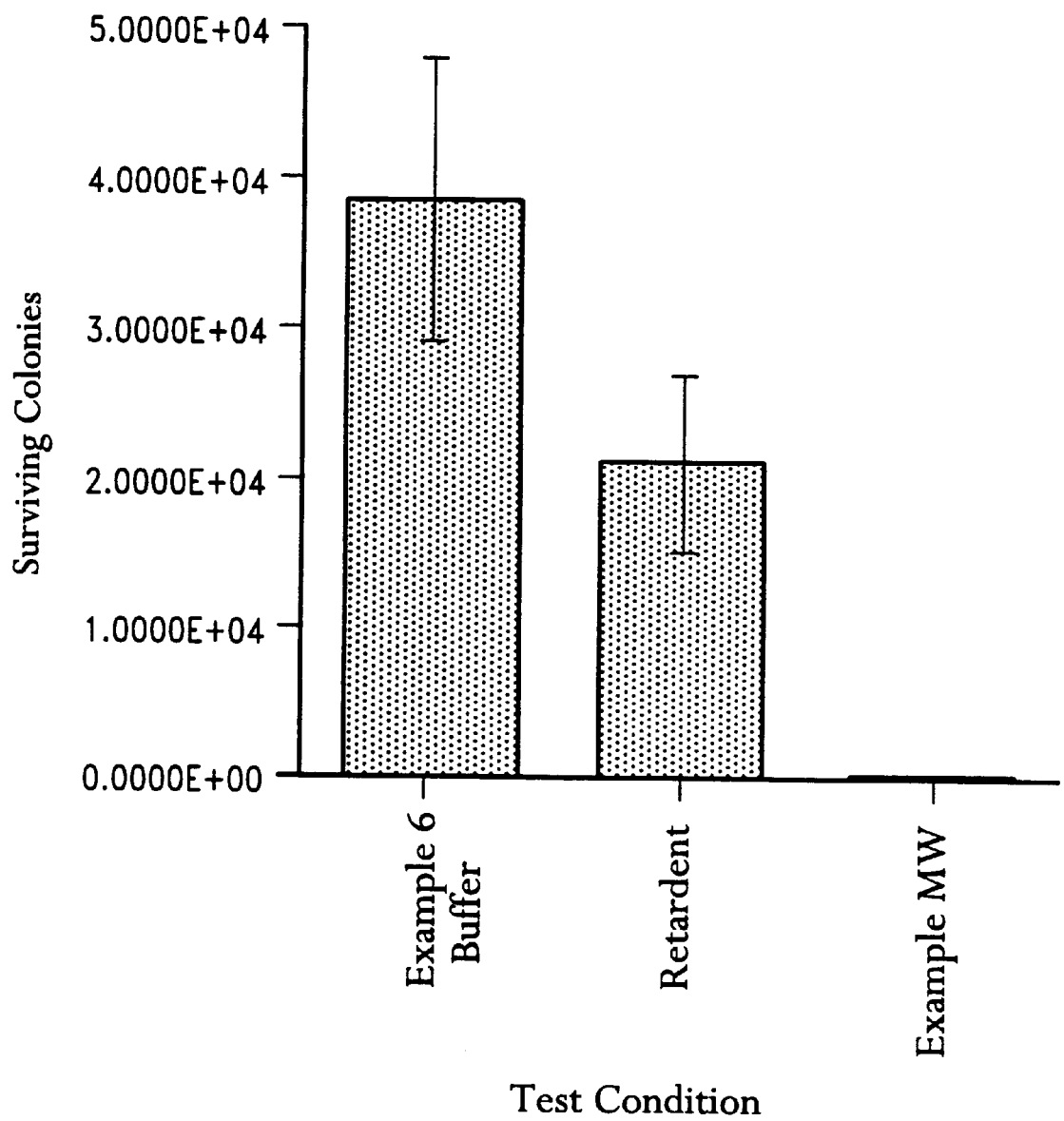
FIG. 5 shows the results of comparative testing of the efficacy of a mouthwash containing a BAC homolog and the efficacy of a commercially available mouthwash (RetarDent).

The results (see FIG. 5) indicate that the example formulation prepared according to Example 6 reduced the number of bacteria normally found in a healthy mouth by about 100%, in contrast to the commercially available RetarDent, which reduced bacteria only by about 50%. Based upon these results, the mouthwash formulation prepared according to Example 6 is much more effective than the commercially-available RetarDent.

Example 9

In Vitro Testing of Comparative Efficacy of Pure BAC Homologs Versus USP BAC Mixtures 1) Hard water conditions A pure homolog (formula I wherein R contains 12 carbon atoms) or a USP mixture (60% $C_{12}$, 30% $C_{14}$, and 10% $C_{16}$; BARQUAT, available from Lonza Chemicals) was dissolved in a 1.0 molar magnesium chloride solution (extremely "hard water" conditions), to achieve a final concentration of 1.88% (weight/weight) of the BAC.

*Pseudomonas aeruginosa* was grown to a cell density of 0.5 McFarland in TSB medium, and 10 microliters of the culture was inoculated into a solution of homolog or USP mixture BAC. The culture was allowed to incubate for 5 minutes. Following incubation, 100 microliters of each solution was transferred to 1 milliliter of a growth medium (Letheen Broth) containing BAC-inactivating compounds (lecithin and polysorbate). Twenty microliters of the medium was then transferred to a TSA agar plate, and allowed to grow at 37° C. overnight. Colony counts were made 24 hours later.

In the USP mixture, 11 colonies survived. In the $C_{12}$ homolog, 234.8 colonies survived. These results indicate that the antimicrobial effectiveness of the $C_{12}$ BAC homolog is approximately 20 times lower than that of the USP mixture in the hard water solution. This is in agreement with published information (e.g. Petrocci, A. N., Green, H. A., Merianos, J. J., and Like, B., *Proceedings of the 60th Mid-year Meeting of the Chemical Specialities Manufacturers Association*, 1974), which indicates that a mixture of BAC homologs is required for the maintenance of the activity of most active antimicrobial species.

2) Testing in absence of hard water

The minimum inhibitory concentration (MIC) for effectiveness against *Pseudomonas aeruginosa* (ATCC 9027) was determined in the absence of hard water conditions. Test solutions contained 0.5% (w/w) allantoin, 0.3% BAC component, 0.1% methyl paraben, 0.5% sodium dodecyl sulfate, 3.6% mannitol, 0.2% sodium hypophosphate (buffer), 0.1% sodium EDTA, and 94.7% water. The BAC component was either USP grade used in Example 9(1) or a BAC homolog of the present invention (being either a pure homolog wherein R in the formula I has 12 or 14 carbon atoms, or a 50/50 mixture of said homologs). To form a dilution series, the solution was diluted, in clear water, to the dilutions shown in Table 2.

The MIC was determined by adding 50 microliters of a culture of the microorganism, from a 0.5 McFarland suspension culture maintained in trypticase soy broth (TSB) to 50 microliters of the specified dilution of the BAC solution to form a test solution. Incubation was allowed to continue for 24 hours at 37° C., following which the turbidity of micro titer wells was visually assessed. Wells showing no turbidity were counted as having no growth, while those showing turbidity were counted as having growth. The MIC is the greatest dilution of test solution required to prevent cell growth, i.e., that concentration required to place the cells into a state in which they do not divide but remain viable. Repeat runs were carried out using USP solution.

The results (see Table 2) indicate that solutions containing the $C_{12}$ or $C_{14}$ homolog, or a mixture of $C_{12}$ and $C_{14}$ homologs, have superior antimicrobial activity as compared to the USP grade BAC mixture.

TABLE 2

| | Growth of *Pseudomonas aeruginosa*[+] | | | | | | | |
|---|---|---|---|---|---|---|---|---|
| Fold dilution | None | 2 | 4 | 8 | 16 | 32 | 64 | 128 | 256 |
| $C_{12}$ | − | − | − | − | − | + | + | + | + |
| $C_{14}$ | − | − | − | − | − | − | + | + | + |
| 50% $C_{12}$ 50% $C_{14}$ | − | − | − | − | − | + | + | + | + |

TABLE 2-continued

Growth of Pseudomonas aeruginosa+

| Fold dilution | None | 2 | 4 | 8 | 16 | 32 | 64 | 128 | 256 |
|---|---|---|---|---|---|---|---|---|---|
| USP$_{Run\ 1}$ (MB80) | – | – | + | + | + | + | + | + | + |
| USP$_{Run\ 2}$ (MB80) | – | + | + | + | + | + | + | + | + |

+(Growth is indicated by a "+"; no growth by a "–").

Various modifications of the invention, in addition to those described herein, will be apparent to those skilled in the art from the foregoing description. Such modifications are intended to fall within the scope of the appended claims.

What is claimed is:

1. An antimicrobial, pharmaceutical composition for topical or oral administration, comprising:

a. from about 0.05 to about 5 percent by weight benzalkonium chloride, wherein greater than 90 percent by weight of the benzalkonium chloride is selected from the group consisting of of benzalkonium chloride homologs having the formula:

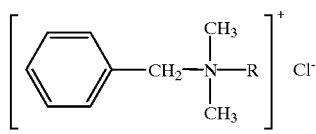

wherein R represents an alkyl side chain of from 12 to 14 carbon atoms;

b. from 0.1–20 weight percent of a surfactant system comprising at least one nonionic surfactant comprising alkanolamine, alkyldimethyl oxide, coconut monoethanolamine, cetyldimethylamine oxide, stearamine oxide, oleamine oxide, or cocamidopropylamine dimethyl oxide; and c. at least about 60 weight percent water.

2. The antimicrobial composition of claim 1 wherein the surfactant system comprises from about 0.05 to about 8 weight percent of the nonionic surfactant.

3. The antimicrobial composition of claim 1 wherein the surfactant system comprises at least one amphoteric surfactant.

4. The antimicrobial composition of claim 3 wherein the surfactant system further comprises at least one amphoteric surfactant comprising cocamido betaine, oleyl betaine, cocamphdiacetate, cocamidopropylhydroxysultaine, or cocamidopropyldimethyl betaine.

5. The antimicrobial composition of claim 1 wherein the surfactant system further comprises at least one cationic surfactant.

6. The antimicrobial composition of claim 5 wherein the surfactant system further comprises at least one cationic surfactant comprising cetyl trimethyl ammonium chloride, trimethyl coco quaternary ammonium chloride, diquaternary polydimethylsiloxane, or trimethyl quaternary ammonium chloride.

7. The antimicrobial composition of claim 1 wherein at least 98 percent by weight of the benzalkonium chloride is selected from the group of benzalkonium chloride homologs having the formula:

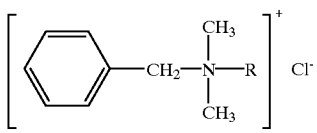

wherein R represents an alkyl side chain of from 12 to 14 carbon atoms.

8. An antimicrobial, pharmaceutical composition for topical or oral administration, comprising:

a. from about 0.05 to about 5 percent by weight benzalkonium chloride, wherein greater than 90 percent by weight of the benzalkonium chloride is selected from the group consisting of of benzalkonium chloride homologs having the formula:

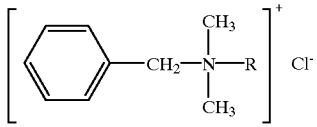

wherein R represents an alkyl side chain of from 12 to 14 carbon atoms;

b. from 0.1–20 weight percent of a surfactant system comprising at least one amphoteric surfactant comprising of cocamido betaine, oleyl betaine, cocamphdiacetate, cocamidopropylhydroxysultaine, or cocamidopropyldimethyl betaine; and c. at least about 60 weight percent water.

9. The antimicrobial composition of claim 8 wherein the surfactant system comprises from about 0.05 to about 8 weight percent of the amphoteric surfactant.

10. The antimicrobial composition of claim 8 wherein the surfactant system further comprises at least one nonionic surfactant.

11. The antimicrobial composition of claim 8 wherein the surfactant system further comprises at least one nonionic surfactant comprising of alkanolamine, alkyldimethyl oxide, coconut monoethanolamine, cetyldimethylamine oxide, stearamine oxide, oleamine oxide, or cocamidopropylamine dimethyl oxide.

12. The antimicrobial composition of claim 8 wherein the surfactant system further comprises at least one cationic surfactant.

13. The antimicrobial composition of claim 8 wherein the surfactant system further comprises at least one cationic surfactant comprising cetyl trimethyl ammonium chloride, trimethyl coco quaternary ammonium chloride, diquaternary polydimethylsiloxane, or trimethyl quaternary ammonium chloride.

14. The antimicrobial composition of claim 8 wherein at least 98 percent by weight of the benzalkonium chloride is selected from the group consisting of of benzalkonium chloride homologs having the formula:

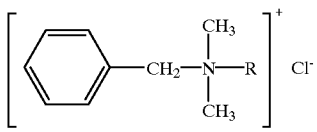

wherein R represents an alkyl side chain of from 12 to 14 carbon atoms.

15. An antimicrobial, pharmaceutical composition for topical or oral administration, comprising:

a. from about 0.05 to about 5 percent by weight benzalkonium chloride, wherein greater than 90 percent by weight of the benzalkonium chloride is selected from the group consisting of of benzalkonium chloride homologs having the formula:

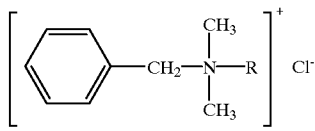

wherein R represents an alkyl side chain of from 12 to 14 carbon atoms;

b. from 0.1–20 weight percent of a surfactant system comprising at least one cationic surfactant comprising cetyl trimethyl ammonium chloride, trimethyl coco quaternary ammonium chloride, diquaternary polydimethylsiloxane, or trimethyl quaternary ammonium chloride; and c. at least about 60 weight percent water.

16. The antimicrobial composition of claim 15 wherein the surfactant system comprises from about 0.05 to about 5 weight percent of the cationic surfactant.

17. The antimicrobial composition of claim 15 wherein the surfactant system further comprises at least one amphoteric surfactant.

18. The antimicrobial composition of claim 15 wherein the surfactant system further comprises at least one amphoteric surfactant comprising cocamido betaine, oleyl betaine, cocamphdiacetate, cocamidopropylhydroxysultaine, or cocamidopropyldimethyl betaine.

19. The antimicrobial composition of claim 15 wherein the surfactant system further comprises at least one nonionic surfactant.

20. The antimicrobial composition of claim 15 wherein the surfactant system further comprises at least one nonionic surfactant comprising alkanolamine, alkyldimethyl oxide, coconut monoethanolamine, cetyldimethylamine oxide, stearamine oxide, oleamine oxide, or cocamidopropylamine dimethyl oxide.

21. The antimicrobial composition of claim 15 wherein at least 98 percent by weight of the benzalkonium chloride is selected from the group of benzalkonium chloride homologs having the formula:

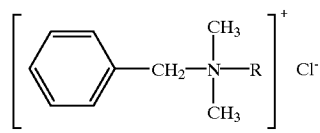

wherein R represents an alkyl side chain of from 12 to 14 carbon atoms.

22. An antimicrobial, pharmaceutical composition for topical or oral administration, comprising:

a. from about 0.05 to about 5 percent by weight benzalkonium chloride, wherein greater than 90 percent by weight of the benzalkonium chloride is selected from the group consisting of of benzalkonium chloride homologs having the formula:

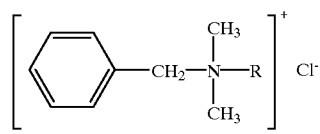

wherein R represents an alkyl side chain of from 12 to 14 carbon atoms;

b. from 0.1–20 weight percent of a surfactant system comprising:
  i. at least one amphoteric surfactant comprising cocamido betaine, oleyl betaine, cocamphdiacetate, cocamidopropylhydroxysultaine, or cocamidopropyldimethyl betaine;
  ii. at least one nonionic surfactant comprising alkanolamine, alkyldimethyl oxide, coconut monoethanolamine, cetyldimethylamine oxide, stearamine oxide, oleamine oxide, or cocamidopropylamine dimethyl oxide; and
  iii. at least one cationic surfactant comprising cetyl trimethyl ammonium chloride, trimethyl coco quaternary ammonium chloride, diquaternary polydimethylsiloxane, or trimethyl quaternary ammonium chloride; and c. at least about 60 weight percent water.

* * * * *